United States Patent [19]

Torii

[11] 4,428,368
[45] Jan. 31, 1984

[54] MASSAGE DEVICE

[76] Inventor: Masakatsu Torii, 40-9, Kamiya 2-chome, Kita-ku, Tokyo, Japan

[21] Appl. No.: 192,101

[22] Filed: Sep. 29, 1980

[51] Int. Cl.$^3$ .............................................. A61H 1/00
[52] U.S. Cl. ..................................... 128/38; 128/24.1
[58] Field of Search ...................... 128/24.1, 24.2, 38, 128/40, 65, 67; 604/313–316

[56] References Cited

U.S. PATENT DOCUMENTS

| | | | |
|---|---|---|---|
| 738,583 | 9/1903 | Watson | 128/38 |
| 1,234,700 | 7/1917 | McLain | 128/41 X |
| 1,308,805 | 7/1919 | Mehrke | 128/24.1 |
| 2,120,872 | 6/1938 | Seward | 128/24.1 |
| 2,168,611 | 8/1939 | Thompson | 128/38 |
| 2,626,601 | 1/1953 | Riley | 128/40 |
| 2,642,863 | 6/1953 | Gordon | 128/38 |
| 3,238,937 | 3/1966 | Stein | 128/40 |
| 3,516,411 | 6/1970 | Adler | 128/24.1 |
| 3,908,642 | 9/1975 | Vinmont | 128/40 |

Primary Examiner—Richard J. Apley
Assistant Examiner—David J. Brown
Attorney, Agent, or Firm—Fisher, Gerhardt, Crampton & Groh

[57] ABSTRACT

This device is constructed in such a manner that a pump for suction and exhaust of air by an electric motor and a crank is provided with a funnel type cup by means of a detachable hose, and an opening portion of the cup is brought into contact with the part of the human body under pressure airtightly. Massage stimulation is performed by the air suction causing the swollen surface of the body and by the air exhaust (discharge) causing the pressure on the surface of the body. Moreover, the cup is provided with an electric heating illuminant to increase the massage stimulation effect by heated air or an electrode for generating low frequency pulse signal.

7 Claims, 16 Drawing Figures

MASSAGE DEVICE

This invention relates to a massage device helping promote the health and the beauty of the body, and more particularly to a massage device applying air suction and pressure alternately on the surface of the body by the utilization of negative pressure and positive pressure of the air.

Heretofore, massage therapy had been such that the muscle of the body was treated by rubbing, kneading, patting or the like by hands to stimulate circulation and increase suppleness, and to obtain recovery of fuctions of the body and the vitality.

However, lately, electric motor drive massage devices became popular. One of the major massage devices is a means for projecting a plunger of a blow attachment elastically by means of a spring when the electric excitation is effected which continuously rub the muscles, and also, another means is a vibrator whose member contacting the body vibrates by polarity change of positive and negative electrodes. These massage means may give a temporary refreshed feeling in the therapy of short time, but they do not give favorable influence on the cellular tissue forming muscle nerve system of the body, and rather there is a question of possible deterioration of the cellular tissue.

An object of this invention is to provide an easy massage by causing the device of this invention to perform the therapy almost similar to the regular massaging methods of rubbing, kneading or the like by the hands in the application of the air suction and exhaust to the muscles to thereby stimulate transitively and to eliminate waste matters by the metabolism, and to obtain recovery of the functions of the body and to remove the subcutaneous fat.

Another object of this invention is to protrude the muscle of the body by suction with negative pressure, and to activate the working of the subcutaneous tissue by the stimulation that does not give adverse influence on the body which is different from the direct blow of the implement.

A further object of this invention is to effect the circulation of blood by alternately causing the contraction and expansion in the subcutaneous muscular and cellular tissue by quickening the application of the negative air pressure and positive air pressure and to exchange the fats and other waste matters with the fresh secretion.

A still further object of this invention is to perform sequential treatments of a plurality of portions of the body to be treated according to the physiological order by providing a plurality of the cup means that applies the air suction and exhaust to the muscle.

A more specific object of this invention is to apply treatment to the body difficult to be treated by the person applying the treatment which is the portion of the body tends to get tired from daily activities in comfortable posture which is free from being forced to take posture or movement accompanied with pains.

A particular object of this invention is to improve the effect of treatment by the massage stimulation with application of the air sucking and pressurizing the muscle by the cup means to thereby facilitate the thermotherapy of the body.

Another and more particular object of this invention is to propose the device for multiplying the massage effect by applying the intermittent electric stimulation with the application of the voltage consisting of low frequency pulse waveforms to the body only when the body is sucked by the cup.

This and other objects of the invention will be apparent from the following descriptions and from the drawings in which.

Figure 1:
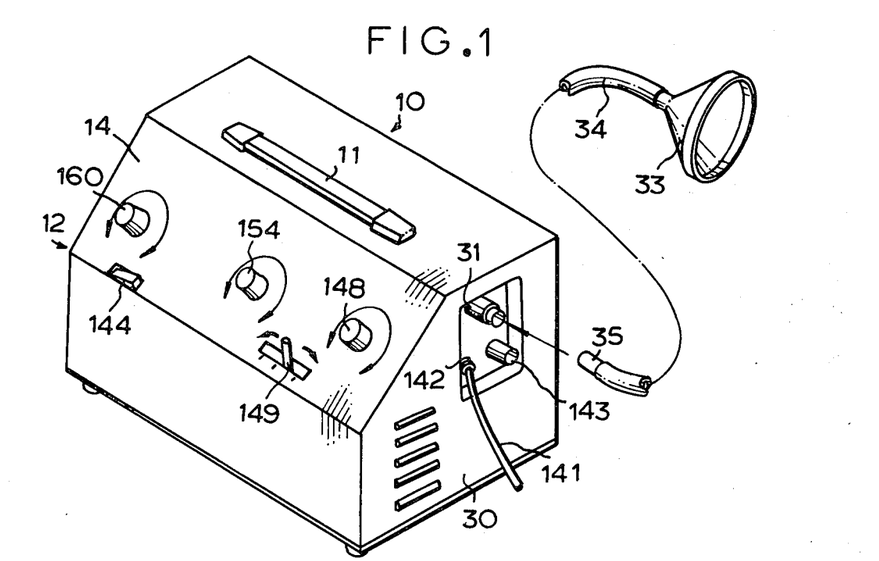
FIG. 1 is a general view perspective of a massage device according to this invention.
Figure 2:
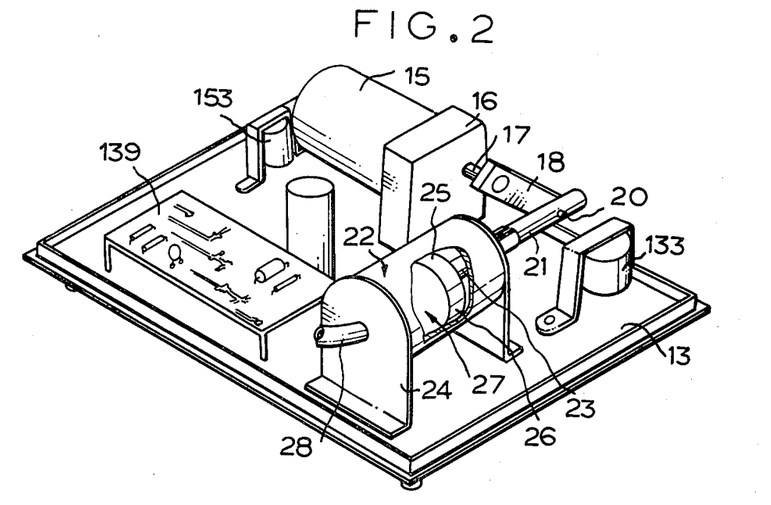
FIG. 2 is a general view perspective of a suction and exhaust drive assembly provided on the bottom wall of the box of the device shown in FIG. 1.

Referring to the drawings, the massage device embodying the invention is designated generally at 10, and the device 10 is housed in an almost square box 12 which can be portable by a handle 11 as shown in FIG. 1. A suction and exhaust assembly shown in FIG. 2 is mounted on a detachable bottom plate 13 of the box 12, and the drive assembly is manipulated by a dial switch or the like to be described hereinafter which is provided with a guage panel 14 of the box 12.

An induction motor 15 is provided on the bottom plate 13, and a crank arm 18 is fixed to the tip of an output shaft 17 of a reduction gear 16 integrally provided with the motor 15, and a base end of a connecting lever 21 is pivotally fixed to a crank pin 20 of the tip of the crank arm 18, and the tip of the connecting lever 21 is connected to a plunger 23 of a pump 22. A cylinder 25 supported by frame plates 24 at both end surfaces is provided on the pump 22, and in the cylinder 25, a suction and exhaust chamber 27 is formed by a piston 26 connected to the plunger to reciprocate therein. On the wall portion of the cylinder forming the suction and exhaust chamber 27, one-way valve may be provided to effect either the suction or exhaust of the air.

A base end of a tube 28 for leading the air outside the box 12 is connected to an end surface of the suction and exhaust chamber of the pump, and its tip is connected to a tubular socket 31 provided in a recessed portion of one side wall of the box 12. A tubular plug 35 of a hose 35 having a cup 33 at its tip is detachably connected to the socket 31.

Figures 3, 4:
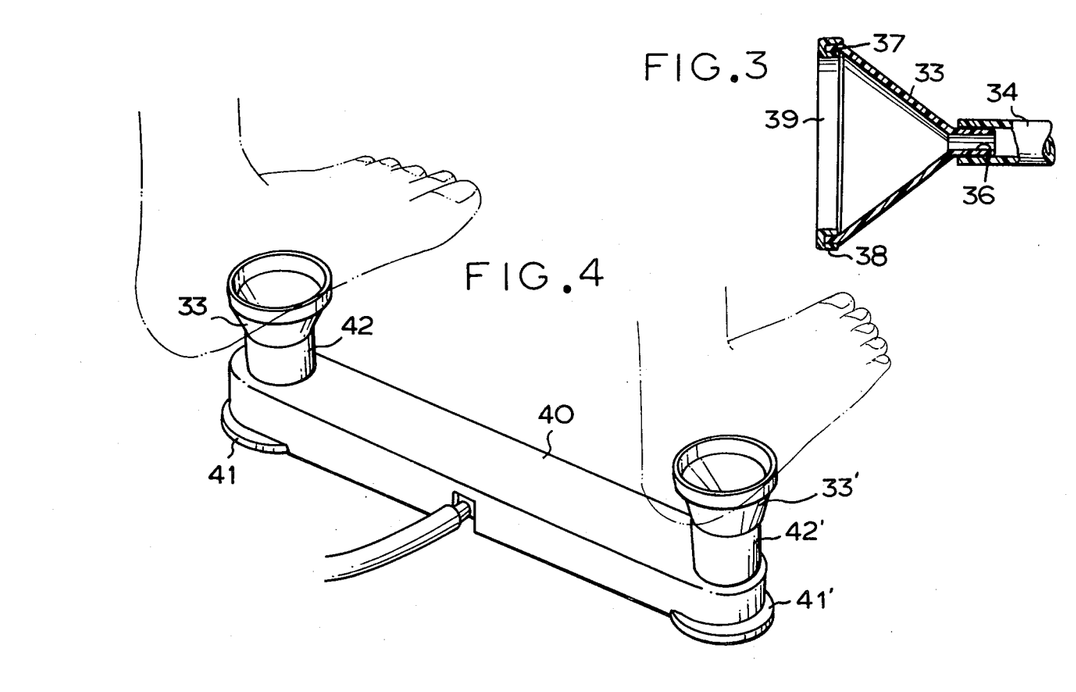
FIG. 3 is an enlarged view cross section of the cup shown in FIG. 1.
FIG. 4 is a view perspective of a base frame supporting a pair of cups to stimulate the bottom surfaces of the soles of both feet simultaneously.

The cup 33 as seen in FIG. 3 is made of synthetic resin material and is generally shaped into a funnel shape, and a connecting portion 36 of its base end portion is pressure fitted to the hose 34, and a buffer ring 39 formed of an annular groove 38 which is made of soft rubber or synthetic resin material is mounted on a peripheral edge flange 37 of the opening portion so as to lightly contact the skin and yet form an air tight seal.

The cup 33 attached with the hose 34 is modified to various embodiments to be suitable for therapy of the symmetrical right and left portions of the body simultaneously or for the therapy of a plurality of portions of the body continuously or for massage by cooperating with the stimulation such as heating, and low frequency voltage or the like.

Figure 5:
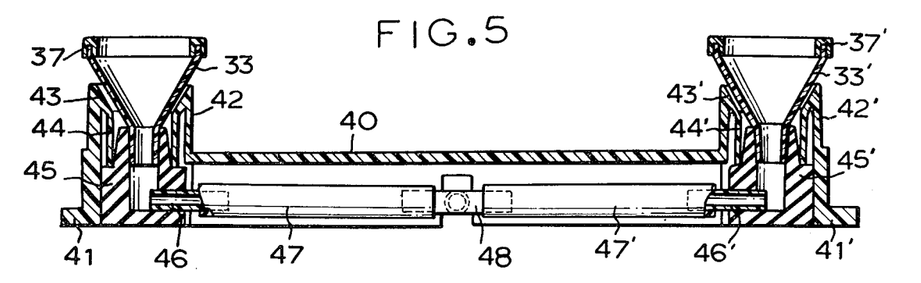
FIG. 5 is a view vertical cross section of FIG. 4.

The embodiment shown in FIG. 4 and FIG. 5 is an assembly for appropriately supporting a pair of cups to massage the soles of both the feet. Namely, lower flange type seat plates 41, 41' and support cylinders 42, 42' risen from the upper surfaces are integrally formed at both end portions of a base frame 40 made of synthetic resin whose cross sectional shape is inverted U-form, and downward cylindrical portions 44, 44' having tapered portions 43, 43' are formed in the lower part of the inside from the upper end peripheral edges of the support cylinders 42, 42', and upper portion small diameter portions of the cylinders 45, 45' made of rubber material with bottoms are pressure fitted to the cylindrical portions 44, 44' from the lower side. The ports 36 of the cups 33, 33' are pressure connected to the cylinders 45, 45'. On the other hand, the inside end portions of the branch hoses 47, 47' which are communicated with the rubber cylinders 45, 45' by means of connecting pipes 46, 46' from the inside of the base frame 40 are connected to the tip of the hose 34 extended from the suction and exhaust drive assembly by means of a T-shaped coupling pipe 48.

The method of use of this device is such that the user sits on the chair and sets his feet on the cups 33, 33' as shown in FIG. 4. The arch of the respective feet is the location where the blood vessel and nerves of the feet are concentrated, and the swelling and compression of the muscles of the portion are alternately repeated by the suction and exhaust actions of the air from the drive assembly, and the fatigue of the nerve of the muscle is recovered by the stimulation, and the function of the vitality of the entire legs is enhanced. At this time, the sole portions in the user's posture of sitting on the chair applied the pressure to the cups so as to be pushed forward and as the result, support cylinders 42, 42' both sides are inclined toward the user, and the pressing force of the sups against the soles of the feet is increased to elevate the stimulation effect.

Figure 6:
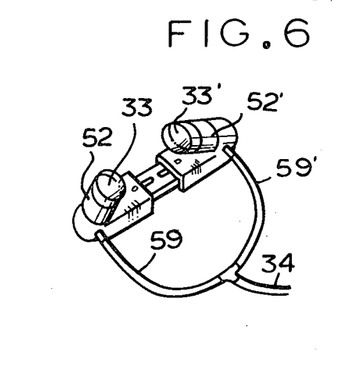
FIG. 6 is a general view perspective of a supporting frame of a pair of cups to stimulate both side portions of the neck portion of the body simultaneously.
Figure 7:
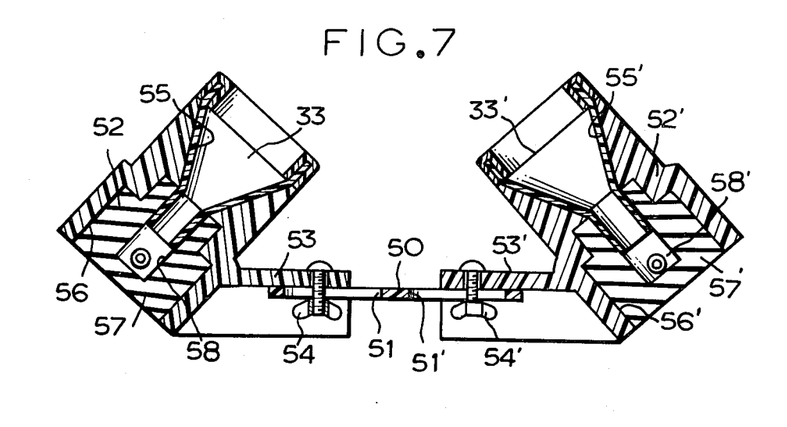
FIG. 7 is a view perspective of the condition of stimulating the back surface of the neck portion by the cup provided on the support frame of FIG. 6.
Figure 8:
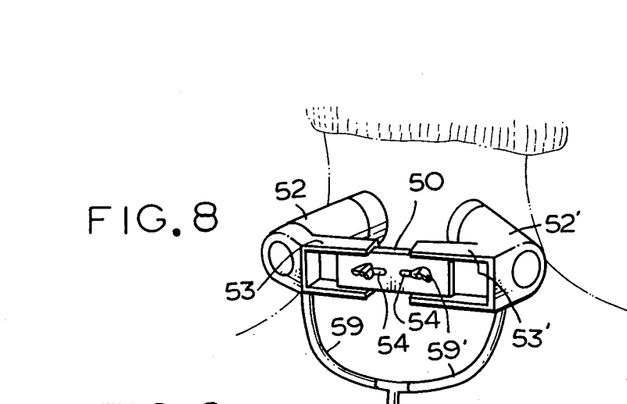
FIG. 8 is a view vertical cross section of the support frame shown in FIG. 6.

FIGS. 6, 7, 8 show the support frame for mounting the pair of cups 33, 33' to stimulate both sides of the back surface of the neck portion. The support assembly is constructed in such a way that a pair of long holes 51, 51' is formed on an elongate connecting plate 50 in its longitudinal direction, and the connecting plate 50 is fixed to connecting members 53, 53' whose cross section is inverted U-shape projecting toward inside from the holding cylinders 52, 52' by means of an interval by thumbscrews 54, 54' so that its interval can be adjusted. The folding cylinders 52, 52' are disposed aslantly toward the inside relative to the connecting members 53, 53', and the inner peripheral surface of the upper portion is formed with tapered portions 55, 55' matched with the cups 33, 33' mounted on the peripheral surface. The lower portion of the tapered portion is formed with circular holes 56, 56' with steps whose diameters are different, and stepped cylindrical connecting members made of rubber or synthetic resin are pressure fitted to the circular holes. The connecting members 57, 57' are formed with the holes portions 58, 58' and the ports 36 of the cups 33, 33' are fitted to the hole portions. The hole portions 58, 58' are connected to the tips of the branch hoses 59, 59' connected to the hose 34. The support frame assembly is used to relieve the head portion from the fatigue by jointly massaging the muscles at both side portions of the muscle of the neck when the neck portion is tired on account of the stiffness or pains in the neck (head) portion, and the interval of both the cups 33, 33' is adjusted by thumbscrews 54, 54' and it is possible to provide an appropriate pressing condition for adults or children.

Figure 9:
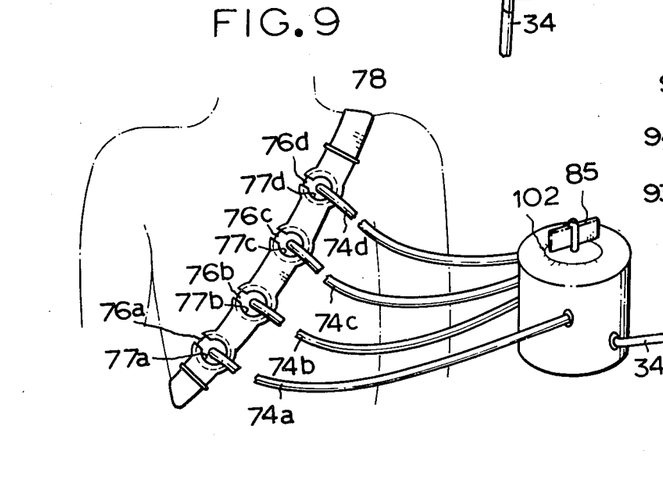
FIG. 9 is a general view perspective of a plurality of cups being simultaneously mounted on the body and a changeover valve assembly for sequentially sending the air to be sucked in and exhausted from the cup group being mounted.
Figure 10:
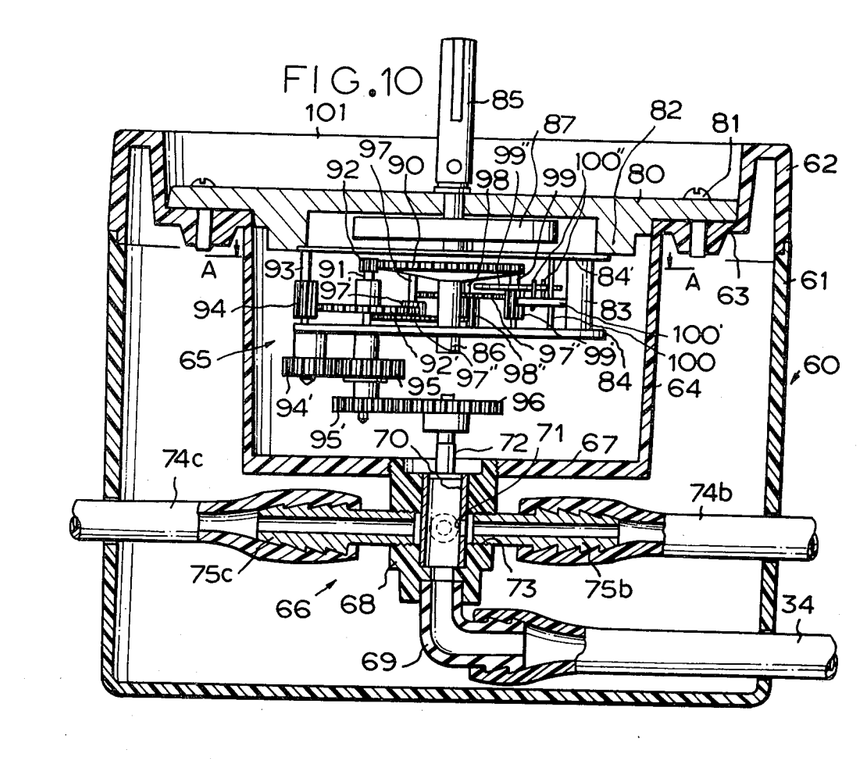
FIG. 10 is a view vertical cross section of the changeover valve assembly and a rotary drive assembly of the valve assembly.
Figure 11:
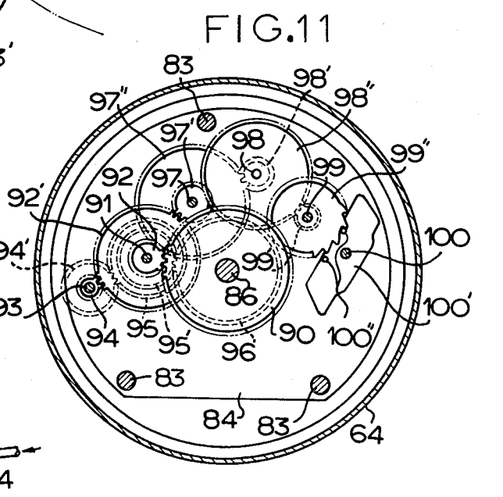
FIG. 11 is a descriptive plan of gear group incorporated into the drive assembly of the valve shown in FIG. 10.

The embodiment shown in FIG. 9 through FIG. 11 is constructed in such a way that an air supply path changeover assembly for suction and discharge from one suction and exhaust drive assembly is interposed in each branch hose having a plurality of cups, and a plurality of cups are mounted on a plurality of locations of the body and the massage is sequentially and repeatedly applied thereto simultaneously.

As shown in FIG. 10, the air supply assembly 60 is housed in a cylindrical box 61 with a bottom. An annular step portion 63 in concave shape is provided on a cover 62 to be mounted on the box 61. A cylindrical inner box 64 coaxially with the box 61 is projectedly provided toward the lower part from the inner peripheral edge of the annular stepped portion 63. A valve assembly 66 is mounted on the lower side of a bottom wall 67 of the inner box 64, and a valve drive assembly 65 for operating the valve assembly is mounted in the inner box 64.

The valve assembly 66 is mounted in the center of the lower surface of the bottom wall of the inner box 64 by means of a cylindrical valve seat 68. At the lower end of the valve seat 68, a plurality of connecting holes 73 (in the embodiment, the mumber is 4 pieces) are radially formed from the inner peripheral surface thereof at the lower end of the valve seat 68 and the connecting holes 73 are screwed to connecting pipes 75a, 75b, 75c, 75d connected to the branch holes 74a, 74b, 74c, 74d. Cups 76a, 76b, 76c, 76d are mounted on each branch hose as shown in FIG. 9. These cup groups are mounted on a band 78 having engaging notched portions 77a, 77b, 77c, 77d so as to be pressure contacted on a plurality of portions of the body.

The valve drive assembly 65 is constructed in such a way that a circular frame plate 80 fitting to the annular step portion 63 of the cover 62 is fixed by means of a screw 81 as shown in FIG. 10, and a pair of circular mounting plates 84, 84' are fixed to the annular projecting portion 82 of the lower surface of the frame plate 80 by means of a support column 83. An operating shaft 86 fixed with a lower end of a wing nut at its upper end portion is pivotally and rotatably fixed to both the mounting plates 84, 84'. The inside end of a spiral coil spring 87 is connected to the lower surface of the frame plate 80 of the operating shaft 86, and its outside end is connected to the annular projecting portion 82 of the lower surface of the frame plate. The wing nut 85 is turned by a desired angle manually and the coil spring 87 is clamped by winding, and the structure of the gear group for equal speed rotation of the output shaft 72 over a desired time by the clamping angle is described as such that a large diameter gear 90 is provided on the lower surface portion of the mounting plate 84' of the operating shaft 86, and a pinion 92 provided on the upper portion of a support shaft 91 is turned by the turning of the gear 90, and a gear 92' of the lower portion is turned. The gear 92' turns a pinion 94 of the support shaft 93, and a gear 94' provided on the lower portion of the support shaft 93 turns a gear 96 integral with the output shaft 72 by means of a pair of transmitting gears 95, 95' which are free from the support shaft 91. On the other hand, in order to turn the gear 96 by a predetermined number of times in a predetermined time, the gear 92' is meshed with a pinion 97' of the support shaft 97, and a gear 97'' provided coaxially with pinion 97' turns a pinion 98' of a support shaft 98 and a gear 98'' provided coaxially with the pinion 98' turns a pinion 99' of a support shaft 99. A ratchet gear 99'' provided coaxially with the pinion 99' turns the output shaft 72 and the valve 70 at a predetermined speed by means of the ratchet gear 99'' in spite of the clamping of the spring 87 by a pair of barlike pawls 100'' provided on a temp plate 100' of the support shaft 100. A cover 101 is fixed to an upper peripheral edge of the cover 62 and a graduation is engraved on the cover 101 to indicate the degree of winding of spring 87 of the spring motor. One full turn of screw 85 which forms the control means for the spring motor results in 15 minutes of operation and shorter periods of time can be selected. The gear ratio is such that valve 70 integral with the output shaft 72 rotates 15 times for one full turn of thumb screw 85. The piston of the pump 22 reciprocates 60–80 times per minute so that each cup of the four cups illustrated in FIG. 9 sucks and pressurizes the body 15 to 20 times per minute.

When the plural cups connected to the valve assembly are used as seen in FIG. 9, portions from the shoulder to the waist can be massaged sequentially without holding the cups. Moreover the valve assembly 65 can be actuated manually for a time desired by the user without relying on electric means dangerous to the body.

Figure 12:
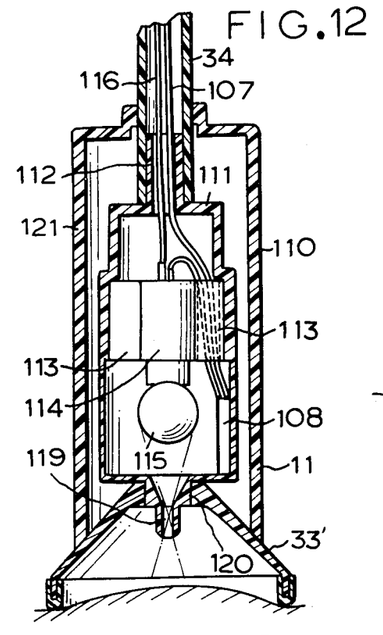
FIG. 12 is a general view vertical cross section of the thermotherapy cup formed by internally installing an electric illuminating heat generator in the base end portion of the cup.

The embodiment shown in FIG. 12 is such that the radiation energy (electromagnetic waves) of the lamp is irradiated to the portions of the surface of the skin to be sucked and pressurized by the cups, and the thermotherapy treatment can be performed by the heated air sucked and discharged.

Namely, the tip of the hose 34 provided and the suction and exhaust assembly is connected to a port 112 projected on the end wall 111 of the base portion of a cylindrical inner box 110. A socket 114 is disposed in the center portion of the inner box 110 by means of a platelike mounting member 113 fixed to the corresponding surface of the inner peripheral wall, and a lamp 115 is screwed to the socket 114. A lead wire 116 for supplying the electric power to the socket 114 is housed and wired in the hose 34, and is connected to the plug 35 made of metal, and the plug 35 is connected to an electric circuit to be described hereinafter which is disposed in the one side wall by means of the socket 31 provided on the box 12 of the drive assembly connected to the plug 35. The other lead wire 107 is connected to the connected terminal (not shown) disposed in the socket 31 and to the barlike connecting terminal (not shown) provided in the plug 35. The other terminal of the lead wire 107 is connected to the socket 114 by interposing the thermostat 108 provided on the inner surface of the peripheral wall of the box. The other terminal of the lead wire 107 is connected to the thermostat 108 provided on the inner surface of the peripheral wall of the inner box and is connected to the socket 114.

A small diameter portion of the base end of the cup 33' is fixed to the step portion 120 of the opening 119 of the nozzle provided at the tip portion of the inner box 110. A cylindrical outer box 121 for reinforcement of the inner box 110 is mounted on the cup 33'.

In case of the embodiment in relation to the lamp 115, the electric power of about 24 V and 0.25 ampere is made to flow, and the thermal stimulation is applied to the portions of the body being subjected to the suction and pressure by the radiation energy transmitted from the lamp. On the other hand, the body is heated by the thermal air sucked in and discharged which remains in the inner box 110 to thereby produce a therapeutic and relaxing effect as well as being useful for beauty treatments.

Figure 13:
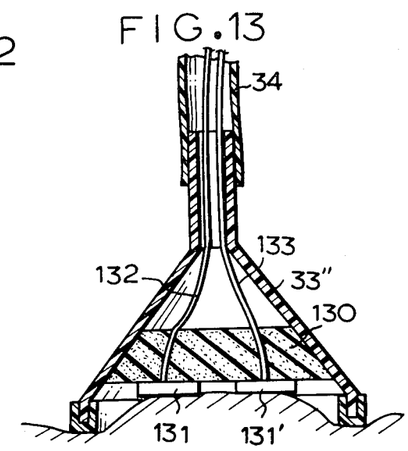
FIG. 13 is a view vertical cross section of the cup formed by installing the electrode of the low frequency pulse electric circuit internally.
Figure 14:
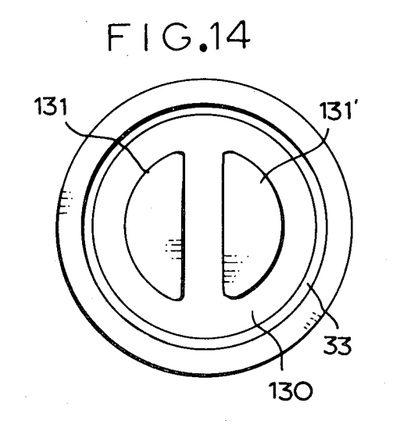
FIG. 14 is a bottom surface view of FIG. 13.

The embodiment shown in FIG. 13 and FIG. 14 is provided with a pair of electrodes for flowing the low frequency electric current to the cups for sucking and pressurizing the required portions of the body to thereby apply the electric stimulation together with the massage.

In FIG. 13, the tip of the hose 34 connected to the suction and exhaust drive assembly is connected to the port portion of the cup 33. An electrode support 130 made of rubber or sponge material of synthetic resin is mounted on the inner surface of the peripheral wall of the cup. The support 130 is of a circular thick type and its peripheral edge tapered portion is fixed to the surface of the inner peripheral wall of the cup. A pair of semicircular electrode plates 131, 131' are mounted on the surface of the support 130. The electrode plates 131, 131' are made of electrically conductive rubber material to which metal powder is mixed. A pair of lead wires 132, 133 connected respectively to the reverse surfaces of the electrode plates 131, 131' are housed and disposed in the hose 34, and are connected to an electric circuit to be described hereinafter.

The low frequency electric current of needlelike pulse waveform generating between both the electrodes is made to flow to the blood vessel and the nerve of the muscle through the skin, and to impart the stimulation for recovery of the functions of tired or sick people. This therapy multiples the effect of the massage through the sucking and pressurizing actions applied to the required portions of the body.

Figure 15:
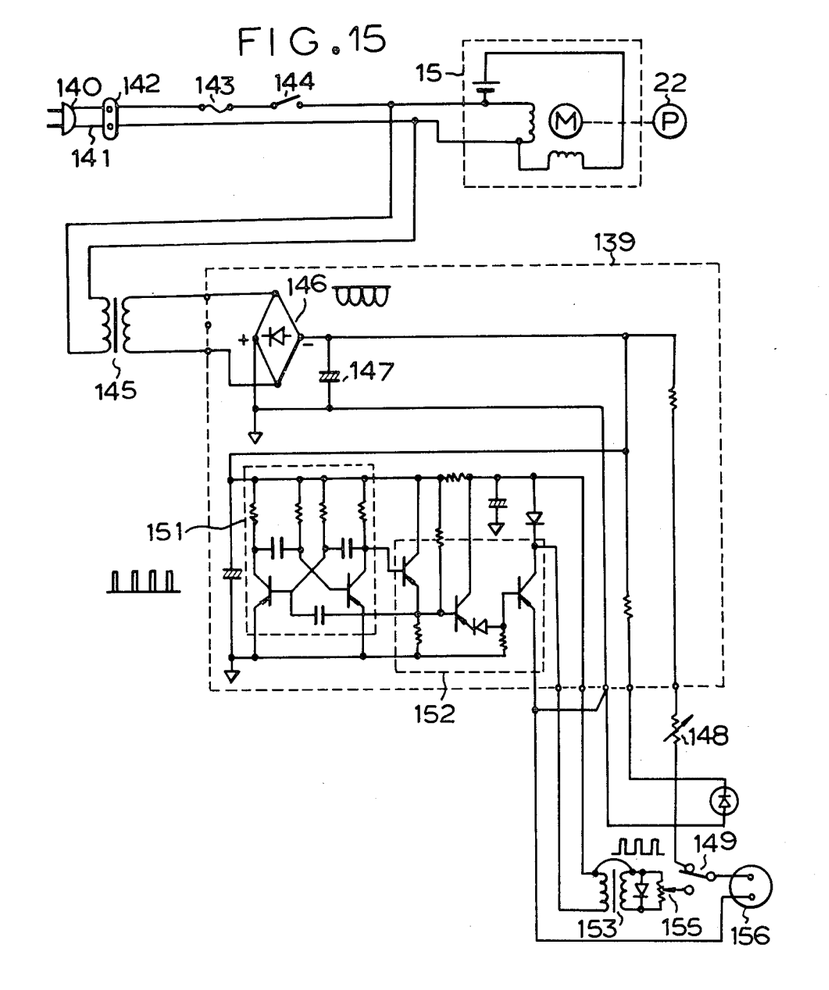
FIG. 15 is a description view of the electric circuit that operates the massage device of this invention.

FIG. 15 shows one embodiment of the electric circuit for operating the device of this invention. In the drawings, in order to connect to the AC power source in the room, the cord wire 141 provided with plug 140 is connected to an induction motor 15 by means of a connector 142, an earth 143, and a power source switch 144 of gauge panel provided on the side wall of the box.

This motor 15 drives the pump 22 by means of the reduction gear 16 and the crank.

On the other hand, the AC power led from the cord 141 is caused to drop its voltage by means of a transformer 145, and then full wave rectification is effected by a diode bridge circuit 146 provided on a print board 139, and this current is transformed to a minus smooth DC waveform by means of a capacitor 147, and the electric current consisting of the DC waveform is connected to an electrode terminal 156 provided in the socket 31 described hereinbefore by means of a variable resistor 148 and a changeover switch 149 to be operated by a dial 148 on the gauge panel.

The electric current of the socket 31 is supplied to the lamp 115 of the heat cup 33' shown in FIG. 12 to be connected detachably. The temperature of the air sucked and exhausted and the temperature of the radiation energy are adjusted by the dial 148.

The minus DC current generated by the diode bridge circuit 146 and the capacitor 147 is formed to the needlelike pulse waveform signal in a low frequency oscillation circuit consisting of astable multivibrator.

This low frequency pulse waveform signal is applied and its electric current is amplified by a buffer circuit 152, and then the voltage is boosted by a transformer 153. The output signal of the transformer 153 is supplied to the changeover switch 149 by means of a variable resistor 155 that operates by a dial 154 on the gauge panel, and reaches an electrode terminal 156 disposed in the socket 31. When the plug 35 of the low frequency cup 33" is fitted to the socket 31, the barlike electrode terminal mounted in the plug 35 is connected automatically to the terminal 156, and the lead wire is inserted through the hose 34 and the needlelike pulse waveform signal of low frequency is supplied from both the electrode plates 131, 131' in the cup 33" to the body thereby the stimulation is applied to the body. This electric signal is fed back from the electrode plate of both the electrode plates 131, 131' by means of the lead wire, plug 35, socket 31. In the meantime, the dial 154 operates the variable resistor 155, and the electric current quantity of the low frequency pulse waveform signal is controlled, and the degree of the stimulation pain applied to the body is adjusted. The changeover switch 149 performs the changeover of the electric current by tilting it either in right or left direction depending on the use of either the thermal cup 33' and the low frequency cup 33" is used. In case, the suction and pressure of the air only are applied without using both of them, it is disposed at upright neutral position.

Figure 16:
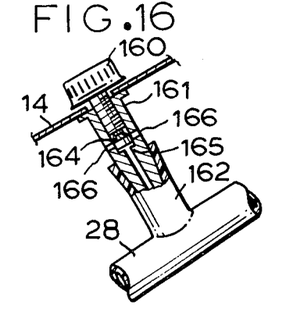
FIG. 16 is a view partially cut-away cross section of a release valve with dial interposed in the tube through which the air for adjustment of the pneumatic pressure to be sucked or discharged passes.

A dial 160 mounted on the gauge panel 14 is provided for adjustment of the pressure of the sucked or exhausted air. As shown in FIG. 16, a base end of a pipe coupling 161 is fixed to the inner surface of the gauge panel 14, and its tip is fitted to a branch tube 162 of the tube 28. A male thread valve shaft 163 of the dial 160 is screwed to a female thread portion of the pipe coupling 161. A valve 164 of the tip of the valve shaft 163 contacts a valve seat 165 of step form of the pipe coupling 161 which is separable by the rotation thereof, and a pair of through holes 166 communicating with the atmosphere are provided on the peripheral wall of the valve seat 165. This provides a variable orifice valve in which the gas passing capacity of the through hole 166 is adjusted by turning the dial, and when the exhaust pressure of the pump 22 is high, the part is discharged from the pressure air through hole 166, and when the suction pressure is high, the atmosphere is introduced through the hole 36. As described in the foregoing, the degree of the suction and pressure of the air to the portions of the body which are in tight contact with the cups can be adjusted, and the stimulation massage appropriate to individual's need can be performed.

What is claimed is:

1. A massage device comprising: a housing, an electric motor, a reduction gear and a crank all connected in series for rotation in unison, a pump connected to the crank and operable to move air, a delivery tube for conveying air moved by said pump to the exterior of the housing, a hose having one end detachably connected to said delivery tube, a rotary valve assembly connected to said hose in fluid communication therewith, a plurality of branch hoses connected with said valve assembly, drive means including a spring motor operative independently of said electric motor for driving said rotary valve assembly, control means rotatable to a maximum of one revolution to initiate said spring motor and being movable to a selected position to determine the period of time of rotation of said rotary valve assembly, said valve assembly being continuously rotatable during said selected period of time to deliver fluid sequentially to said plurality of branch hoses simultaneously with the movement of air by said pump, a plurality of cups connected to said plurality of branch hoses, respectively, and band means attachable to the body of a person and having notched portions for detachably receiving and holding said cups in selected spaced relationship relative to each other and for locating said cups in a plurality of spaced locations on the body to sequentially apply stimulation to such locations for the predetermined period of time.

2. The combination of claim 1 wherein a one-way valve is provided on the peripheral wall of the operation chamber of the pump, and either operation of the sucking or the exhausting (discharging) of the air only is performed.

3. The combination of claim 1 wherein said delivery tube forms an opening communicating with the atmosphere, and a variable orifice valve communicating with said opening for variably regulating the size of the opening communicating with the atmosphere and the amount of the air flowing in said delivery tube.

4. The combination of claim 1 wherein a cylindrical housing is interposed between a base end portion of each cup and said branch hoses, an electrical heating element in said housing and a source of DC electrical power connected in circuit with said heating element.

5. The combination of claim 4 wherein a variable resistor is interposed in the DC electric circuit, and the temperature of the heating element is adjusted by dial manipulation of the variable resistor.

6. The combination of claim 1 wherein an electrode support made of sponge having air permeating property and insulating property is mounted in a conical inner peripheral wall of the cup, and a pair of electrode plates are mounted on the surface of the electrode support, and said electrical support is connected with a source of DC electrical current, the DC electric current is converted by a rectifier and is transformed to a needlelike pulse waveform signal, and the pulse waveform signal is supplied to the electrode plates.

7. The combination of claim 6 wherein a variable resistor is interposed in the needlelike pulse waveform signal circuit, and its output is adjustable.

* * * * *